US00PP30416P3

(12) United States Plant Patent
Randag

(10) Patent No.: US PP30,416 P3
(45) Date of Patent: Apr. 16, 2019

(54) CALLA LILY PLANT NAMED 'BRASILIA'

(50) Latin Name: *Zantedeschia sprengeri*
Varietal Denomination: Brasilia

(71) Applicant: Sunglory Beheer B.V., Schagerbrug (NL)

(72) Inventor: Cecilius Jan-Jochem Randag, 't Zand (NL)

(73) Assignee: Sunglory Beheer B.V., Schagerbrug (NL)

( * ) Notice: Subject to any disclaimer, the term of this patent is extended or adjusted under 35 U.S.C. 154(b) by 0 days.

(21) Appl. No.: 15/732,672

(22) Filed: Dec. 13, 2017

(65) Prior Publication Data

US 2018/0177113 P1 Jun. 21, 2018

Related U.S. Application Data

(60) Provisional application No. 62/498,157, filed on Dec. 15, 2016.

(51) Int. Cl.
*A01H 5/02* (2018.01)

(52) U.S. Cl.
USPC ..... Plt./490
CPC ..... *A01H 5/02* (2013.01)

(58) Field of Classification Search
USPC ..... Plt./490
See application file for complete search history.

*Primary Examiner* — Annette H Para
(74) *Attorney, Agent, or Firm* — The Webb Law Firm

(57) ABSTRACT

'Brasilia' is a new variety of calla lily plant having inflorescences with a white-colored spathe having a pink flush that produces 5-25 inflorescences per tuber. The height of the top of an inflorescence above the soil can reach up to 40 cm. The leaves are green with transparent maculations present and have a leathery texture.

2 Drawing Sheets

Botanical classification: *Zantedeschia sprengeri*.
Varietal denomination: 'Brasilia'.

BACKGROUND OF THE NEW PLANT

The present invention comprises a new and distinct cultivar of calla lily, botanically known as *Zantedeschia sprengeri* and hereinafter referred to by the cultivar name 'Brasilia'.

'Brasilia' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as C02001 (female parent, unpatented) with a *Zantedeschia sprengeri* variety named 'Odessa' (male parent, U.S. Plant Pat. No. 18,833). 'Brasilia' was selected in 2007 by the inventor in 't Zand, The Netherlands as one flowering plant within the progeny of the stated cross.

The first act of asexual reproduction of 'Brasilia' by tissue culture was performed by the inventor in September of 2013 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S.

Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Brasilia' which, in combination, distinguish this calla lily as a new and distinct cultivar:

1. White-colored spathes with a pink flush;
2. Compact plant architecture; and
3. High inflorescence production.

Further, when compared to calla lily plant named 'Snow Storm' (U.S. Plant Pat. No. 28,122), the upper surface spathe color of 'Snow Storm' varies between White Group RHS 155A and 155D, whereas the upper surface spathe color of 'Brasilia' varies between White Group RHS 155A and 155B and has a pink flush that varies between Red Group RHS 54C and 55B.

Table 1 provides similarities and differences of 'Brasilia' to its parents, *Zantedeschia sprengeri* selection C02001 and *Zantedeschia sprengeri* variety 'Odessa'.

TABLE 1

| 'Brasilia' | Similarities | Differences |
|---|---|---|
| C02001 | Spathe shape<br>Number of inflorescences | Spathe color<br>Plant height |
| 'Odessa' | Leaf shape<br>Spathe size<br>Number of florescences | Spathe color |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
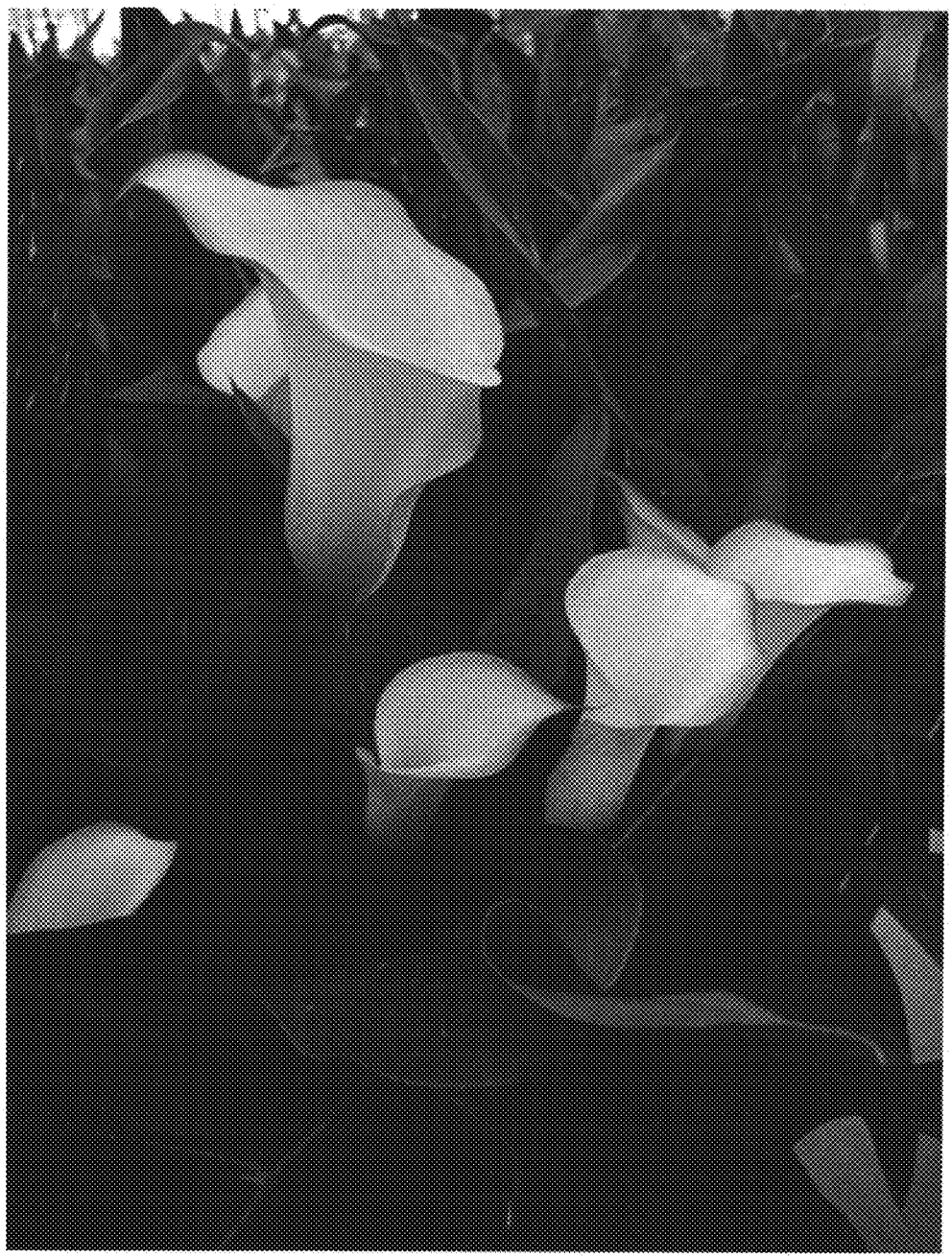
FIG. 1 is a close-up photograph of a plant of the new variety.
Figure 2:
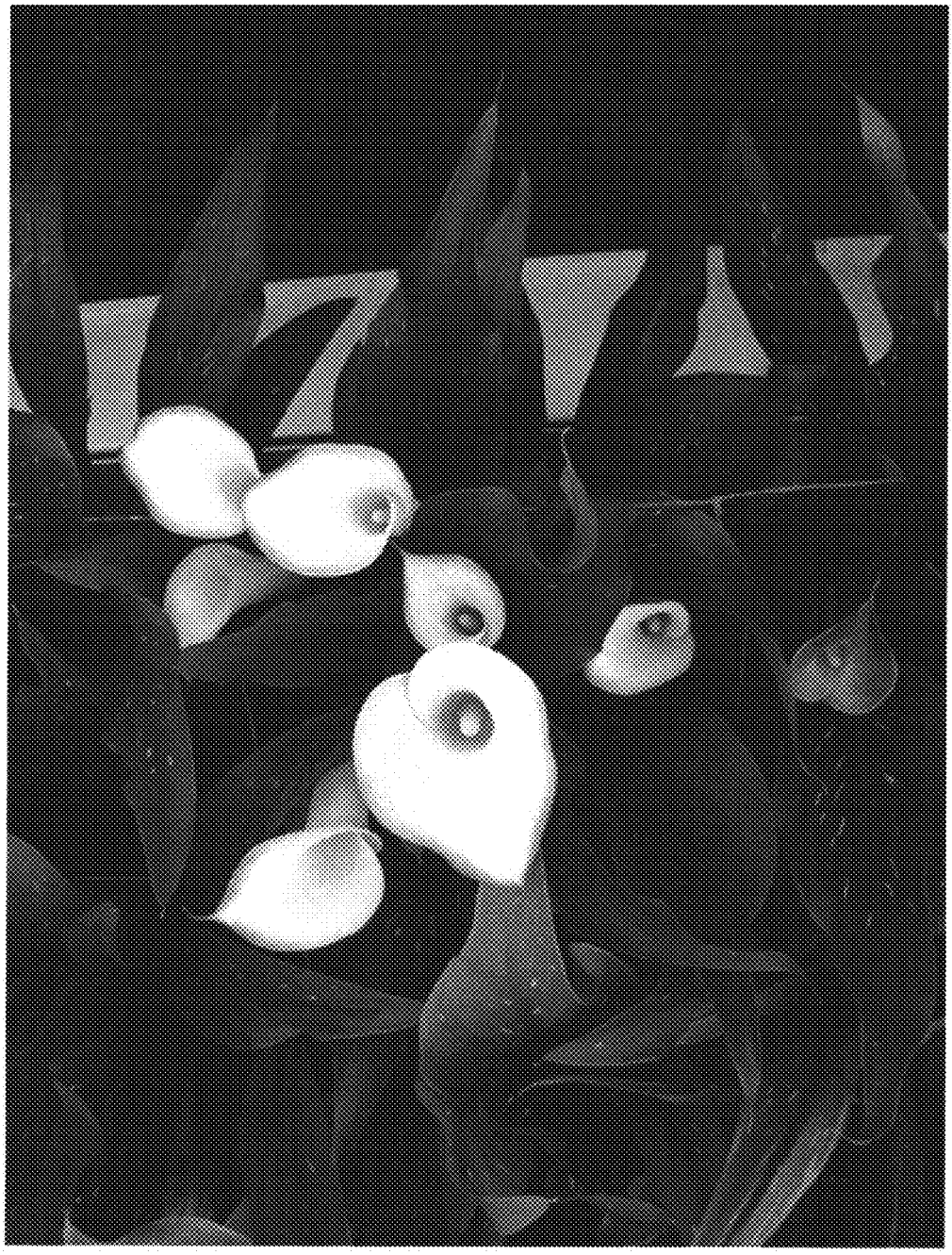
FIG. 2 is a photograph of a top view of a plant of the new variety.

The plant:

*Size.*—Height of the leaf canopy above the soil: 16-36 cm. Height of top of inflorescences above the soil: 14-40 cm. Diameter: 9-11 cm.

*Form.*—Erect.

*Number of inflorescences per tuber.*—Size 14-16 cm in diameter: 5-9 inflorescences. Size 16-18 cm in diameter: 10-12 inflorescences. Size 18-20 cm in diameter: 10-20 inflorescences. Size 20+ cm in diameter: 11-25 inflorescences.

*Branches.*—Average Number: 7.6. Color: Between Yellow-Green Group RHS 144A and 144B.

*Leaves.*—Size: Width: 2-7 cm. Length: 10-23 cm. Number per plant: 16-32. Shape: Lanceolate. Apex: Apiculate. Base: Attenuate. Margin: Undulate; having a color between Green Group RHS 137A and Yellow-Green Group RHS 145A. Color: Upper surface: Yellow-Green Group RHS 146A to 147B, having transparent maculations of approximately White Group RHS 155A. Lower surface: Green Group RHS 137A to Yellow-Green Group RHS 147A, having transparent maculations of approximately White Group RHS 155A. Veins: Configuration: Pinnate. Color: Upper Surface: Yellow-Green Group RHS 146C to 146D. Lower Surface: Green Group RHS 137A to 137B. Surface quality: Leathery. Petiole: Length: 6-13 cm. Diameter: 4-9 mm. Color: The base is White Group RHS 155A, the upper part is Green Group RHS 143A to 143B.

*Roots.*—Color: White. Branching: Similar to other *Zantedeschia* varieties.

The inflorescence and seeds:

*Spathe.*—Size: Length (measured from opening to tip): 4.5-6.5 cm. Width: 3.5-5.5 cm. Height: 6-10 cm. Color: Upper surface: Varies between White Group RHS 155A and 155B and has a pink flush that varies between Red Group RHS 54C and 55B. Lower surface: Varies between White Group RHS 155A and 155B and has a pink flush that varies between Red Group RHS 54B and 55A. Vein color: Between Red Group RHS 54A and 55B. Shape: Funnel. Apex: Apiculate. Base: Attenuate. Margin: Undulate. Texture: Smooth (upper and lower surfaces).

*Spadix.*—Size: Length: 25-35 mm. Diameter: 5-9 mm. Color: Between Yellow Group RHS 10A and 12B. Position relative to spathe: Upright.

*Peduncle.*—Size: Length: 15-36 cm. Diameter: 5-9 mm. Color: The upper part is between Green Group RHS 143A and Yellow-Green Group 144A, the lower part is Green-White Group RHS 157C. Texture: Smooth.

*Reproductive organs.*—Location of female organs: Basal position of the spadix. Location of male organs: Upper position of the spadix. Perianth: Conspicuous. Stamens: Presence: Not visible before pollen release. Number: More than 20. Pollen amount: Abundant; similar to 'Picasso' (U.S. Plant Pat. No 15,282). Color: Between White Group RHS 155A and 155B. Anther: Shape: Round. Length: Less than 1 mm. Color: Between Yellow Group RHS 10A and 12B. Filament: Length: Less than 1 mm. Color: Between White Group RHS 155A and 155B. Pistils: Number: 15 to 30. Length beyond perianth: About 1 mm. Stigma: Shape: Round. Size: Less than 1 mm. Style: Length: Less than 1 mm. Color: Between Yellow Group RHS 10D and 12C. Ovaries: Texture: Smooth. Length: Between 1 to 10 mm. Width: Between 1 to 10 mm. Color: Top color is between Yellow-Green Group RHS 145C and 145D, the bottom color is between White Group RHS 155B to Green-White Group RHS 157C.

*Seeds.*—Length: 4-7 mm. Width: 3-6 mm. Color: Between Yellow-Green Group RHS 150A and 151A. Amount: Between 1-60.

General:

*Disease resistance.*—No unusual susceptibility to diseases noticed to date.

*Pest resistance.*—No unusual susceptibility to pests noticed to date.

*Heat tolerance.*—No heat tolerance.

*Hardiness.*—Not hardy.

*Flowering.*—In general, the time from planting to first flowering takes eight weeks. However, tubers stored for a longer period before planting may flower earlier — up to five weeks after planting.

*Lastingness.*—About two weeks on the plant.

*Fragrance.*—None.

I claim:

1. A new and distinct variety of calla lily plant named 'Brasilia' as herein described and illustrated.

* * * * *